United States Patent [19]

Liboff et al.

[11] Patent Number: 5,067,940

[45] Date of Patent: * Nov. 26, 1991

[54] METHOD AND APPARATUS FOR CONTROLLING THE GROWTH OF CARTILAGE

[75] Inventors: Abraham R. Liboff, Birmingham, Mich.; Bruce R. McLeod, Bozeman, Mont.; Stephen D. Smith, Lexington, Ky.

[73] Assignee: Life Resonances, Inc., Bozeman, Mont.

[ * ] Notice: The portion of the term of this patent subsequent to Jun. 12, 2007 has been disclaimed.

[21] Appl. No.: 265,265

[22] Filed: Oct. 31, 1988

Related U.S. Application Data

[63] Continuation-in-part of Ser. No. 172,268, Mar. 23, 1988.

[51] Int. Cl.$^5$ ................................................ A61N 2/04
[52] U.S. Cl. ........................................ 600/13; 600/15; 128/419 F
[58] Field of Search ............................ 600/13, 14, 15; 128/419 F

[56] References Cited

U.S. PATENT DOCUMENTS

| | | |
|---|---|---|
| 109,783 | 10/1887 | Liboff et al. . |
| 3,890,953 | 6/1975 | Kraus et al. . |
| 3,893,462 | 7/1975 | Manning . |
| 3,911,930 | 10/1978 | Hagfers et al. . |
| 3,952,751 | 4/1976 | Yarger . |
| 4,105,017 | 8/1978 | Ryaby et al. . |
| 4,266,532 | 5/1981 | Ryaby et al. . |
| 4,428,366 | 1/1984 | Findl et al. . |
| 4,459,988 | 7/1986 | Madurski . |
| 4,535,775 | 8/1985 | Brighton et al. . |
| 4,561,426 | 12/1985 | Stewart . |
| 4,600,010 | 7/1986 | Dugot . |
| 4,616,629 | 10/1986 | Meere . |
| 4,622,953 | 11/1986 | Gordon . |
| 4,654,574 | 3/1987 | Thaler . |
| 4,683,873 | 8/1987 | Cadossi et al. . |
| 4,932,951 | 6/1990 | Libaff et al. ........................... 600/13 |

OTHER PUBLICATIONS

"Interactions Between Electro-Magnetic Fields and Cells", Chiabrera, et al., Plenum Publishing, 1985, pp. 281-291.

"A Role for the Magnetic Field in the Radiation-Induced Efflux of Calcium Ions from Brain Tissue in Vitro", Bio-Electriomagnetics 6:327 337, 1985.

"Geomagnetic Cyclotron Resonance in Living Cells", Journal of Biological Physics, vol. 13, 1985.

Primary Examiner—Kyle L. Howell
Assistant Examiner—John Hanley
Attorney, Agent, or Firm—Dykema Gossett

[57] ABSTRACT

An apparatus and method for regulating the growth of cartilage in vivo are provided. The apparatus includes a magnetic field generator and a magnetic field detector for producing a controlled, fluctuating, directionally oriented magnetic field parallel to a predetermined axis projecting through the target tissue. The field detector samples the magnetic flux density along the predetermined axis and provides a signal to a microprocessor which determines the average value of the flux density. The applied magnetic field is oscillated at predetermined frequencies to maintain a preselected ratio of frequency to average flux density. This ratio is maintained by adjusting the frequency of the fluctuating magnetic field and/or by adjusting the intensity of the applied magnetic field as the composite magnetic flux density changes in response to changes in the local magnetic field to which the target tissue is subjected. By maintaining these precise predetermined ratios of frequency to average magnetic flux density, growth characteristics of the target cartilage are controlled.

6 Claims, 3 Drawing Sheets

METHOD AND APPARATUS FOR CONTROLLING THE GROWTH OF CARTILAGE

This application is a continuation-in-part of U.S. patent application Ser. No. 172,268 filed Mar. 23, 1988.

FIELD OF THE INVENTION

The present invention relates generally to methods and apparatus for controlling growth characteristics of living tissue. More specifically, the present invention relates to non-invasive techniques for controlling the growth, maintenance and repair of cartilaginous connective tissue.

BACKGROUND OF THE INVENTION

Tissue and cell development have been studied extensively to determine the mechanisms by which maturation, maintenance, and repair occur in living organisms. Generally, development of a cell or tissue can be considered as a transformation from one state or stage to another relatively permanent state or condition. Development encompasses a wide variety of developmental patterns, all of which are characterized by progressive and systematic transformation of the cells or tissue.

In many instances it is desirable to control or alter the development of cells and tissue in vivo to enhance the quality of life for higher organisms such as man. To this end, science has struggled to provide means by which the natural order of an organism can be maintained or restored in defiance of a debilitating injury, disease or other abnormality. While some prior art therapies have been successful, others have failed to reach their full potential due to unwanted side effects, inferior results, or difficult implementation.

As will be appreciated by those skilled in the art, tissue and organ development involve complex processes of cellular growth, differentiation and interaction mediated by complex biochemical reactions. At the genetic level, development is regulated by genomic expression; at the cellular level, the role of membrane interaction with the complex biochemical milieu of higher organisms is instrumental in developmental processes. Moreover, "remodeling" of tissues or organs is often an essential step in the natural development of higher organisms.

In recent years, multidisciplinary investigations of developmental processes have provided evidence suggesting that electric and magnetic fields play an important role in cell and tissue behavior. In U.S. patent application Ser. No. 923,760, entitled, "Techniques for Enhancing the Permeability of Ions," which has been assigned to the assignee of the present invention and the disclosure of which is incorporated herein by reference, a method and apparatus are disclosed by which transmembrane movement of a preselected ion is magnetically regulated using a timevarying magnetic field. The fluctuating magnetic field is preferably tuned to the cyclotron resonance energy absorption frequency of the preselected ion. This important discovery brought to light the interplay of local geomagnetic fields and frequency dependence in ion transport mechanisms. It has now been discovered that by utilizing and extending the principles of cyclotron resonance tuning, an unexpected and remarkable advance in the control and modification of developmental processes in living tissue can be achieved. In U.S. patent application Ser. No. 172,268 filed Mar. 23, 1988, the disclosure of which is incorporated herein by reference, the inventors of the present invention disclose that cyclotron resonance can be used to control tissue development. In our U.S. patent application entitled "Method and Apparatus For Controlling the Growth of Non-Osseous, Non-Cartilaginous, Solid Connective Tissue," filed Oct. 6, 1988, Ser. No. 254,438, a method of controlling the growth of non-osseous, non-cartilaginous, connective tissue is disclosed which utilizes cyclotron resonance frequencies. In the present application, we disclose a method and apparatus for affecting the growth characteristics of cartilage.

Currently, research efforts in the area of electronic medical devices which affect growth mechanisms in living systems have focused on strain-related bioelectrical phenomena that have been observed in tissue such as bone, tendon and cartilage. During the last few decades, others have noted that electrical potentials are produced in bone in response to mechanical stress. It has been postulated that these electrical potentials mediate the stress-induced structural changes in bone architecture which were observed almost a century ago by J. Wolfe. Hence, although bioelectrical potentials are not well understood, numerous attempts have been made to induce tissue growth with electrical potentials and currents. Much of this research has dealt with the repair of bone non-unions, i.e. bone fractures which have not responded to traditional therapies. Some experimentation has been carried out by others on the effects of electrical stimulation of cartilage, particularly articular cartilage, in an effort to increase the rate of growth and repair of damaged cartilage.

As will be appreciated by those skilled in the art, there are various types of cartilaginous tissues. These are typically classified as hyaline cartilage, fibrocartilage and elastic cartilage. Hyaline cartilage has a matrix comprised of mucopolysaccharide in which chondrocytes are present in lacunae. Collagen fibers are dispersed in the matrix to a limited extent. In fibrocartilage, the matrix is interlaced with prominent collagen fiber bundles and the chondrocytes are more widely scattered than in hyaline cartilage. Elastic cartilage contains a network of elastic fibers which are histologically similar to elastin fibers. Hyaline cartilage is the most abundant cartilaginous tissue in humans and is present in primary cartilaginous joints where it unites two sections of bone. Most articular cartilage is hyaline cartilage. Secondary cartilaginous joints are formed by discs of fibrocartilage which join vertebrae in the vertebral column. As with other connective tissues, the formation of cartilaginous tissue is a complex biological process, involving the interaction of cells and fibers in a biochemical milieu.

A number of conditions are known in which the integrity of cartilage is compromised. Traumatic injury may occur by which the cartilage is disrupted, for example at articular surfaces. A number of degenerative diseases are also known in which general erosion of cartilaginous tissue occurs along with the appearance of fissures. Regeneration of damaged cartilage is a slow process.

A considerable amount of experimentation has been conducted in which the electrical environment of tissue has been altered in an attempt to stimulate tissue growth. These efforts originally concentrated on the use of electrode implants by which direct current was flowed across or into a bone non-union or abnormal union to stimulate repair of bone or articular cartilage. Due to numerous drawbacks, including the associated risks of surgery required to implant the electrodes, alternate, non-invasive techniques were pursued. While capacitively-generated electrostatic fields provided some beneficial results, the relatively large fields necessary were generally prohibitive. Finally, alternating, high-intensity electromagnetic fields were utilized to induce a voltage in bone. It was believed that by using the affected bone as a conductor, current flow through the bone could be induced which would produce therapeutic benefits.

Two typical prior art inductive devices are disclosed in U.S. Pat. No. 3,893,462 to Manning entitled, "Bio-electrochemical Regenerator and Stimulator Devices and Methods for Applying Electrical Energy to Cells and/or Tissue in a Living Body" and in U.S. Pat. No. 4,105,017 to Ryaby et al. entitled, "Modification of the Growth Repair and Maintenance Behavior of Living Tissue and Cells by a Specific and Selective Change in Electrical Environment." These investigators have focused on the use of large pulsed magnetic fields to produce moderately high induced currents in living tissue with well-defined "therapeutic" waveforms. In the area of regeneration of damaged cartilage, the work of Baker et al, which is disclosed in the article, "Electrical Stimulation of Articular Cartilage Regeneration," *Annals New York Academy of Sciences*, illustrates the direct electrical stimulation of tissue using an implanted bimetallic electrode to enhance regrowth of damaged articular cartilage. Therein, defects were created in the articular cartilage of the lateral femoral condyles of rabbits. The bimetallic electrodes were inserted into holes drilled through the condyle flares with a platinum wire from the electrode extending through the condyle at the defect and projecting slightly from the condyle surface. Both in vivo and in vitro experiments were carried out by Baker in this manner. A constant voltage was then applied for a period of from one to nine weeks. When compared with the control animals, the experimental animals demonstrated an increase in cellular proliferation and matrix production at the defect with regeneration of articular cartilage.

Pulsing electromagnetic fields have also been used experimentally to alter articular cartilage. In "Effects of Pulsing Electromagnetic Fields on Bone Growth and Articular Cartilage," Smith et al., *Clin. Orthop. and Related Res.*, Vol. 181, exposure of immature rabbits to pulsing electromagnetic fields produced a significant increase in femoral articular cartilage glycosaminoglycan.

The inventors of the present invention have approached the problem of regulating cartilage growth from a different perspective. In its preferred embodiment, the present invention utilizes the interaction of fluctuating magnetic fields and preselected ions present in biological fluids to influence developmental processes. It should also be noted that although a possible role of magnetic fields beyond the galvanic action of induced currents is briefly mentioned in U.S. Pat. No. 3,890,953 to Kraus et al., to Applicants' knowledge no investigator has previously controlled cartilage growth in the manner set forth in the present invention.

SUMMARY OF THE INVENTION

In one aspect, the present invention provides an apparatus for controlling the growth of tissue, particularly the growth of cartilaginous tissue. The novel apparatus includes magnetic field generating means such as a field coil for generating a controlled, fluctuating magnetic field which penetrates the cartilaginous tissue in a human or animal subject and an associated magnetic field sensing device for measuring the intensity of the magnetic field present in the cartilaginous tissue. In one embodiment, the magnetic field generating means and magnetic field sensor are enclosed within a housing along with a power source such as a battery or the like. In operation, the magnetic field generating means is positioned adjacent a region of living cartilaginous tissue in a subject, the growth characteristics of which are to be controlled. A fluctuating, directional magnetic field is then generated by the magnetic field generating means. The applied magnetic flux density is directed along a predetermined axis which passes through the cartilaginous tissue to be affected. In one embodiment, the applied magnetic flux density along the axis is superimposed on that component of the local or ambient magnetic field which is parallel to the predetermined axis to create a fluctuating composite field. The resultant combined magnetic flux density which is parallel to the predetermined axis and which passes through the cartilaginous tissue to be affected is measured by the magnetic field sensor. The magnetic field sensor determines the net average value of the magnetic flux density which passes through the target tissue along the predetermined axis. In one embodiment, the frequency of the fluctuating magnetic field is set at a predetermined value and the net average value of the magnetic flux density is then regulated by adjusting the magnitude of the applied magnetic field to produce a combined magnetic field having a preselected ratio of frequency-to-field magnitude which affects the growth characteristics of the cartilaginous tissue. In a preferred embodiment, changes in the magnitude of the local magnetic field along the predetermined axis which would otherwise alter the magnetic flux density of the combined magnetic field parallel to the predetermined axis and which would thus produce a deviation from the desired ratio are counterbalanced by adjustment of the magnitude of the applied, fluctuating magnetic field. This adjustment is preferably made by microprocessing means in association with both the magnetic field generating means and the magnetic field sensor. Preferred ratios of frequency-to-field magnitude are determined with reference to the equation:

$$f_c/B = q/(2\pi m)$$

where $f_c$ is the frequency of the combined magnetic field in Hertz, B is the non-zero average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla. In one embodiment, the values of q and m are selected with reference to the charge and mass of a preselected ion.

In another embodiment, changes in the ambient magnetic field which would otherwise alter the ratio of frequency-to-magnetic field are counterbalanced by adjusting the frequency of the applied magnetic field to maintain the preferred ratio. The present invention also contemplates the adjustment of both frequency and field magnitude to maintain the predetermined preferred ratio. Preferably, the peak-to-peak amplitude of the AC component is in the range of about $2.0 \times 10^{-7}$ to about $2.0 \times 10^{-4}$ Tesla. The waveform is preferably substantially sinusoidal, but other waveforms are suitable.

The present invention also provides a method of controlling the growth characteristics of living cartilage which includes in one aspect the steps of generating a fluctuating, directionally-oriented magnetic field; positioning a region of living cartilaginous tissur of a human or animal subject within the fluctuating, magnetic field so that the field passes through the target cartilaginous tissue parallel to a predetermined axis that extends through the cartilage; measuring the net average value of the combined magnetic flux density parallel to the predetermined axis through the tissue, where the combined magnetic field is the sum of the local magnetic field along the predetermined axis and the applied magnetic field; adjusting the frequency and/or magnitude of the applied magnetic field to produce a combined magnetic field along the axis having a predetermined ratio of frequency-to-magnitude, where the predetermined ratio influences the growth characteristics of the cartilage; maintaining the predetermined ratio of frequency to magnitude of the combined field; and exposing the cartilage to the combined magnetic field for a period of time sufficient to affect the growth characteristics of the cartilage. Other relationships between frequency and magnitude may be useful or even desirable in a particular application.

The present invention is particularly suitable for enhancing the growth of damaged cartilage such as articular cartilage to facilitate repair. The stimulated growth of cartilage such as that which forms the structures of the human nose is also a preferred aspect of the present invention, and it is anticipated that the present invention will be particularly useful in the growth of cartilage following cosmetic surgery. It is also anticipated that the present invention will be useful in shaping cartilage tissue, such as enlarging a specific region of cartilage to bring about a desired alteration. These and other advantages of the present invention will become more apparent from the following description of preferred embodiments and with reference to the drawings in which:

DETAILED DESCRIPTION OF THE PREFERRED EMBODIMENTS

Figure 1:
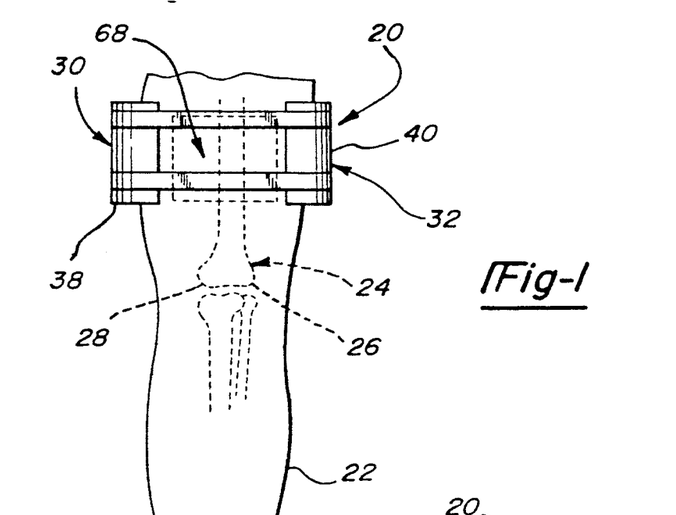
FIG. 1 is a front elevational view of the present invention as applied to the treatment of damaged cartilage.

Referring now to FIG. 1 of the drawings, cartilage growth regulator 20 is shown in position on leg 22 of a human subject. It is to be understood that both the apparatus and the method of the present invention are suitable for use in controlling tissue growth in an animal subject or a human subject. Thus, the target tissue which is to be controlled is a region of living tissue in a subject, or, in other words, an "in vivo" target tissue. As used herein, the term "living cartilage" shall be defined, without limiting its customary meaning, as cartilaginous tissue which is capable of conducting metabolic functions such as cellular respiration and which possesses viable growth characteristics. "Growth characteristics" shall be defined, without limiting its customary meaning, as those attributes of living tissue which serve to mediate replication, growth, maintenance and repair. Although the stimulation of tissue growth will be emphasized in this description of preferred embodiments of the present invention, it is to be understood that the present invention may also be suitable to retard or impede the development of living tissue and may be suitable for such applications as the prevention of abnormal tissue development.

Femur 24 is shown having damaged regions 26 and 28 of articular cartilage, the regeneration of which is to be stimulated by the present invention. As will be appreciated by those skilled in the art, the natural developmental processes by which damaged regions 26 and 28 are repaired is relatively slow and may be interrupted by a factor of known or unknown etiology resulting in delayed healing. In this embodiment, cartilage growth regulator 20 includes two treatment heads 30 and 32 which are positioned on leg 22 in the region of damaged cartilage regions 26 and 28 in the opposed fashion illustrated in FIG. 1. As will be explained more fully, it is important that treatment heads 30 and 32 be placed adjacent the target cartilage such that the tissue is within the range of the magnetic flux generated by the treatment heads. Also, although it is preferred that two treatment heads be employed in an opposed fashion as illustrated in FIG. 1, a single treatment head or a plurality of treatment heads greater than two may be suitable in some applications.

Figure 2:
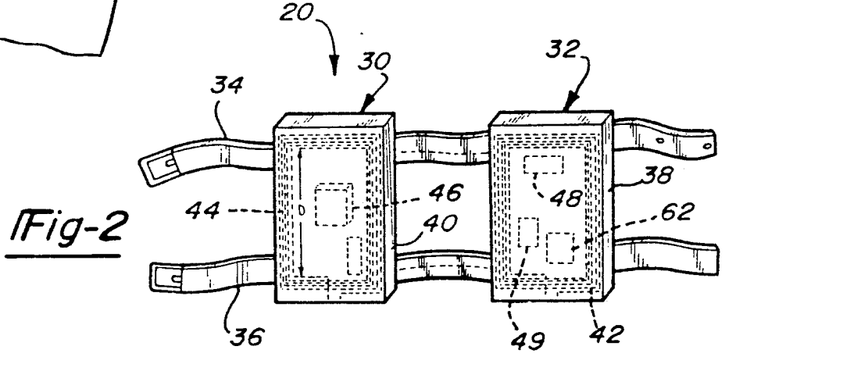
FIG. 2 is a front elevational view of the present invention with two treatment heads having field coils and magnetic field sensing means shown in phantom.

Referring now to FIG. 2 of the drawings, retaining straps 34 and 36 are seen by which cartilage growth regulator 20 is preferably secured into position on leg 22. Other securing means may be suitable or desirable in a particular application. It may also be desirable to provide cartilage growth regulator 20 as a stationary unit or the like as an alternative to the mobile unit depicted in FIGS. 1-3. Straps or belts 34 and 36 are attached to treatment heads 30, 32 by any convenient means, preferably in a manner which allows the distance between treatment heads 30, 32 to be adjusted to be obtain the substantially opposed orientation shown in FIG. 1. Hence, it is preferred that straps 30, 32 permit adjustment sufficient for cartilage growth regulator 20 to be used on limbs of various sizes. Treatment heads 30 and 32 should be snugly but comfortably in position to prevent substantial movement relative to the target cartilage, illustrated here as damaged cartilage regions 26 and 28. It is anticipated that the present invention will be useful in conjunction with conventional plaster or plastic casts wherein cartilage growth regulator 20 may be integrated directly into the cast architecture or may be mounted on the extension of the cast.

Figure 3:
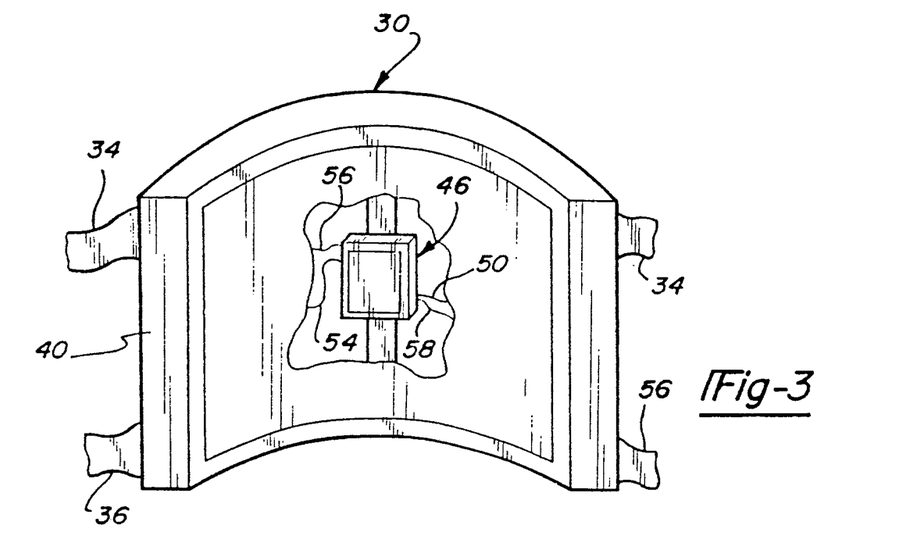
FIG. 3 is a front elevational view of one treatment head of the present invention with the housing broken away to illustrate the magnetic field sensing means.

Referring now to FIGS. 2 and 3, each treatment head 30, 32 includes a housing 38, 40 of a non-magnetic material such as plastic which encloses a field coil 42, 44. In addition, it is preferred that at least one treatment head enclose a magnetic field sensing device 46, such as a Hall-effect device, shown enclosed within housing 40 of treatment head 30. Power source 48 is provided, preferably enclosed within one of the treatment heads. Power source 48 may comprise a dry cell battery or the like. It is preferred that two or more separate power sources be provided to minimize the number of circuit elements required. Housing 38 is also preferably provided with means by which battery 48 can be accessed such as a sliding panel or the like (not shown) to facilitate installation. It may also be suitable to mount battery 48 on the outside of housing 38 or to provide some other external arrangement. While it is a significant feature and advantage of the present invention to provide a tissue growth regulator which includes a self-contained power source, and thus which is both lightweight and mobile, other power sources such as an ac line source may be used in connection with an ac/dc converter where mobility is not required.

Field coils 44 and 42 are the preferred means by which an applied magnetic field is generated in the present invention. The radius of each field coil 44 and 42, as well as the turns of winding, may vary in accordance with the principles of the present invention. Those skilled in the art will appreciate that other electromagnets or possibly permanent magnets may be adapted for use in the present invention and any such use is intended to come within the scope of the present invention. Field coils 44 and 42 are most preferred since they provide a simple means for concentrating magnetic lines of force. Also, the present invention includes several components within a single housing, and therefore shielding may be employed to prevent undesired interactions between components.

Figure 4:
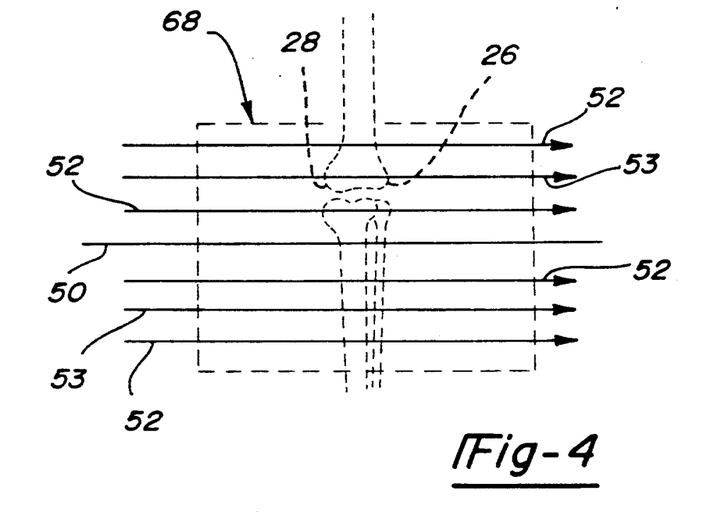
FIG. 4 illustrates the combined magnetic flux.

In the most preferred arrangement, the geometry and relative position of field coils 44, 42 during treatment are such that field coils 44, 42 operate as Helmholtz coils. Those skilled in the art will thus appreciate that in the most preferred arrangement, field coils 44, 42 are substantially identical, field-aiding, parallel coaxial coils separated by a distance equal to the radius of each coil. In this most preferred embodiment, the Helmholtz configuration produces an applied magnetic field in a predetermined space between the coils. Referring to FIG. 4, this predetermined space 68 is occupied by the target tissue, the growth characteristics of which are regulated by the present invention. This concept will be more fully explained herein. Hence, predetermined space 68 is shown through which magnetic field lines 52 extend parallel to predetermined axis 50. Magnetic field lines 52 pass through the target tissue, which is illustrated here as damaged cartilage regions 26, 28.

It will be appreciated that the target tissue will generally be subject to local magnetic influences. As used herein, "local magnetic field" shall be defined as the magnetic influences, including the earth's magnetic field or geomagnetic field, which create a local magnetic flux that flows through the target tissue. "Magnetic flux density" shall be defined in the customary manner as the number of magnetic field lines per unit area through a section perpendicular to the direction of flux. Factors contributing to the local magnetic field in addition to the geomagnetic field may include localized regions of ferromagnetic materials or the like. In one embodiment of the present invention, field coils 42 and 44 are used to create an applied, fluctuating magnetic field which when combined with the local magnetic field parallel to predetermined axis 50 produces a resultant or combined magnetic field having a precisely controlled, predetermined ratio of magnetic flux density to frequency.

Referring now to FIG. 3 of the drawings, magnetic field sensing device or magnetometer 46 is shown in housing 40 with the appropriate leads 54, 56, 58 and 60, by which the field-sensing device is electrically connected to power source 48 and in one embodiment to microprocessing means 62. As will be appreciated by those skilled in the art, the Helmholtz configuration of field coils 42, 44 provides a substantially uniform or equal applied magnetic field in active volume or predetermined space 68 between the coils. Hence, cartilage growth regulator 20 allows a substantially uniform applied magnetic field to be applied to the target tissue in predetermined space 68. The direction of the applied magnetic flux defines the direction of predetermined axis 50. That is, the flux of the applied magnetic field is always in the same direction as predetermined axis 50. In the preferred embodiment of the invention, this applied magnetic flux is superimposed on the local magnetic flux in predetermined space 68. The field lines of this local flux component are shown by reference numeral 53.

Magnetometer 46 is positioned in cartilage growth regulator 20 to measure the total or composite magnetic flux which passes through predetermined space 68 parallel to predetermined axis 50. It will be understood, then, that magnetometer 46 is provided to measure the composite magnetic field along axis 50. The local field component either augments or decreases the applied magnetic flux unless the local field component is zero. This is an important feature of the present invention. The relatively low applied flux densities and precise predetermined relationships of combined flux density and frequency provided by the present invention must be maintained during treatment, notwithstanding the influence of the local magnetic field. This is achieved in essentially two preferred manners which will be explained more fully herein. Thus, magnetometer 46 is provided to determine the magnitude of the magnetic flux density of the local magnetic field. Hence, in one embodiment of the invention, predetermined space 68 is occupied by a region of living cartilage of a human or animal subject. Predetermined axis 50 which projects through predetermined space 68 and thus through the target tissue is defined by the relative position of cartilage growth regulator 20 with respect to the target tissue. Predetermined axis 50 is in the same direction as the applied magnetic flux generated by field coils 42, 44 through predetermined space 68. During this procedure, magnetometer 46 measures the total magnetic flux density parallel to predetermined axis 50 which passes through the target tissue. This total or composite magnetic flux density is the sum of the applied component and the local component. The local component may at times be in the same direction as the applied flux and at other times be in directions other than the applied flux. At times the local component may also be zero. These changes in the local component along the axis are produced by changes in the direction of predetermined axis 50 as cartilage growth regulator 20 is repositioned such as when an ambulatory patient receiving treatment moves leg 22. Thus at $T_1$ the applied flux generated by field coils 42, 44 may be parallel to a north-south axis, perhaps when the patient faces west. Since the direction of predetermined axis 50 is defined by the direction of the applied flux, in this position, predetermined axis 50 is therefore also in the north-south direction. At $T_2$, the patient may turn to the north causing a 90 degree rotation of field coils 42, 44 such that the applied magnetic flux is now parallel to an east-west axis. Accordingly, predetermined axis 50 is then also in the east-west direction. In most cases, the local component will be different in different directions; hence, the composite flux measured by magnetometer 46 along predetermined axis 50 will change in response to changes in the position of cartilage growth regulator 20 with respect to the local magnetic field. The net average value of magnetic flux density is accordingly regulated to adjust to the change in composite flux. Therefore, cartilage growth regulator 20 is preferably a mobile unit which is a significant advantage.

Figure 5:
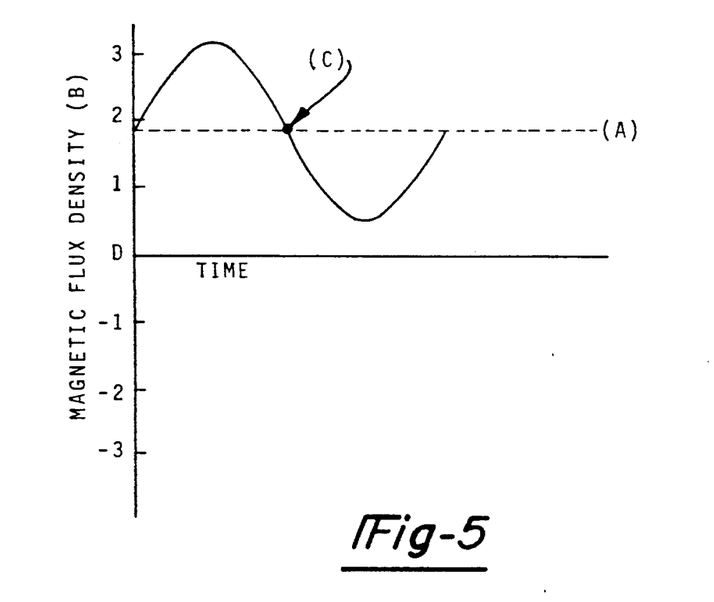
FIG. 5 illustrates the fluctuating, non-zero average value of the combined magnetic flux density.

The unexpected and superior results of the present invention are achieved by creating a fluctuating combined or composite magnetic field having a magnetic flux density parallel to predetermined axis 50, where the combined magnetic flux density along axis 50 is maintained at a predetermined relationship to the frequency of the fluctuations. In this embodiment, the combined magnetic flux density parallel to predetermined axis 50 has a non-zero net average value. As illustrated in FIG. 5 of the drawings, the therapeutic magnetic field of the present invention can be thought of as a static field having reference level A on which a fluctuating magnetic field is superimposed. It comprises an ac component which varies in amplitude but not direction and a dc reference around which the ac component varies. Reference level A is the non-zero average value of the flux density (B). Therefore, it will be understood that the non-zero average or net average value of the composite magnetic flux density along predetermined axis 50 is utilized since the magnitude B of the composite flux density changes at a predetermined rate due to oscillation or fluctuation of the applied magnetic flux. Thus, an average value is utilized which is a non-zero average value illustrated at point (c). This reflects that although the composite magnetic flux density along the axis is oscillating at a controlled rate, the composite field is regulated by the intensity of the applied field to ensure that the composite field is always unipolar; that is, the composite field is always in the same direction along predetermined axis 50.

As stated, it has been found that rather precise relationships of the flux density of the combined magnetic field to the frequency of the fluctuations are used in the present invention to provide therapeutic results. These ratios of frequency to composite flux density are found in accordance with the following equation:

$f_c/B = q/(2\pi m)$ where $f_c$ is the frequency of the combined magnetic field in Hertz, B is the net average value of the magnetic flux density of the combined magnetic field parallel to predetermined axis 50 in Tesla, q/m has a value of from about $5 \times 10^5$ to about $100 \times 10^6$ Coulombs per kilogram. B preferably has a value not in excess of about $5 \times 10^{-4}$ Tesla. To stimulate growth of cartilage, as an example, the following frequency and associated combined magnetic flux density (B) is preferred:

| fc (Hertz) | B (Tesla) |
|---|---|
| 16.0 | $12.68 \times 10^{-6}$ | at an ac amplitude, peak-to-peak of 15 microTesla rms.

Another preferred relationship for stimulating cartilage growth is:

| fc (Hertz) | B (Tesla) |
|---|---|
| 50.5 | $4.00 \times 10^{-5}$ | at an ac amplitude, peak-to-peak of 15 microTesla rms.

While the exact mechanism by which growth characteristics of the target cartilage tissue are affected by the present invention is not fully understood, as will be explained more fully in connection with the method of the present invention, remarkable results are achieved by tuning the combined field to resonant absorption frequencies of preselected ions.

Therefore, it will be readily understood by those skilled in the art that cartilage growth regulator 20 includes in one aspect a magnetic field generating means for providing an oscillating magnetic field parallel to a predetermined axis. Cartilage growth regulator 20 also preferably includes magnetic field sensing means by which the magnetic flux density parallel to the predetermined axis is measured. A microcontrolling means is also preferably provided in cartilage growth regulator 20 by which a predetermined relationship between the magnetic flux density parallel to the predetermined axis and the frequency of the magnetic field oscillation is created and maintained as cartilage growth regulator 20 changes orientation with respect to the local magnetic field. Cartilage growth regulator 20 is thus used to create, monitor and adjust a magnetic field of predetermined parameters in predetermined volume 68. While this predetermined relationship is preferably maintained by adjusting the applied flux to compensate for changes in the local field component, alternatively the frequency can be adjusted to preserve the desired ratio.

In use, cartilage, preferably hyaline cartilage, fibrocartilage, or elastic cartilage is placed within predetermined volume 68 and is then subjected to a fluctuating magnetic field as described for a period of time sufficient to properly influence the growth characteristics of the target tissue. In the most preferred embodiment, this influence will comprise the acceleration of growth characteristics to cause the proliferation and growth of cartilage by causing matrix deposition and and chondrocyte proliferation. In addition, it may be possible to retard growth. While the length of time necessary for successful treatment may vary, it is anticipated that up to about 100 days of treatment of damaged cartilage will provide beneficial results. Longer treatment may be desirable in certain applications.

In another embodiment of the present invention, values for q and m are determined with reference to a preselected ionic species. It will be known by those skilled in the art that the biochemical milieu of cartilage comprises a mixture of various ions in the intercellular and interstitial fluid. These ions include potassium ions, magnesium ions, sodiums ions, chloride ions, phosphate ions, sulfate ions, carbonate ions, bicarbonate ions and the like and various ions formed by the dissociation of amino acids, proteins, sugars, nucleotides and enzymes. Applicants have found that by utilizing the values of charge and mass for a preselected ion in the equation set forth above, which will be recognized by those skilled in the art as the cyclotron resonance relationship solved for $f_c/B$, ratios of frequency to magnetic flux density can be determined which serve to regulate growth characteristics of living cartilage in accordance with the present invention. Evidence to date indicates that by using the charge-to-mass ratio of a preselected ion, a specific cyclotron resonance frequency for the ion can be determined. By then tuning cartilage growth regulator 20 to maintain a combined magnetic flux density having the proper cyclotron resonance frequency, living tissue containing the preselected ion can be treated to bring about changes in growth characteristics. Again, evidence indicates that the beneficial results of the present invention in this embodiment are achieved when the preselected ion absorbs energy from the magnetic field of the present invention having the desired parameters. It is believed that this increase in energy promotes the transmembrane movement of the preselected ion across the cell membrane of one or more cell types comprising the target tissue. By enhancing the transmembrane movement of preselected ions in this manner, cell growth and tissue development can be increased or decreased by the present invention. For increasing the growth of cartilage, it is preferred that the preselected ion comprise $Ca^{++}$ or $Mg^{++}$. To retard or inhibit bone growth, it is preferred that the preselected ion comprise $K^+$. Harmonics of these values may also be suitable.

It will be appreciated by the prior explanation of preferred embodiments of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 68 which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. For example, if it necessary to maintain a frequency of 16 Hz and an average flux density of $1.26 \times 10^{-5}$ Tesla to affect growth characteristics of the target tissue, changes in the local field which would otherwise cause unwanted deviations in the combined magnetic flux density must be corrected by increasing or decreasing the applied magnetic flux density accordingly. This is most preferably performed by the microcontroller in connection with both the field generating means and the field-sensing device. Alternatively, as stated, if changes in the combined magnetic flux density along the axis will occur due to changes in the orientation of cartilage growth regulator 20 with respect to the local magnetic field, the frequency of the oscillations can then be changed so that the preferred therapeutic ratio is maintained. Once again, it is important to realize that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Referring now to FIG. 2 of the drawings, each field coil 42, 44 preferably has up to about 3000 turns or loops of conducting wire, the diameter d of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention.

It is also to be understood that the applied magnetic field which results in a combined magnetic flux density along predetermined axis 50 may be produced by a sinusoidal signal or from a full-wave rectified signal applied to field coils 42, 44. It may also be appropriate in some instances to reduce components of the local magnetic field which are not parallel to predetermined axis 50 to zero through the use of additional coils positioned at right angles to treatment heads 30, 32 to create an opposite but equal field. It may also be suitable to reduce the local magnetic field component to zero throughout treatment using additional coils or the like.

Figure 6:
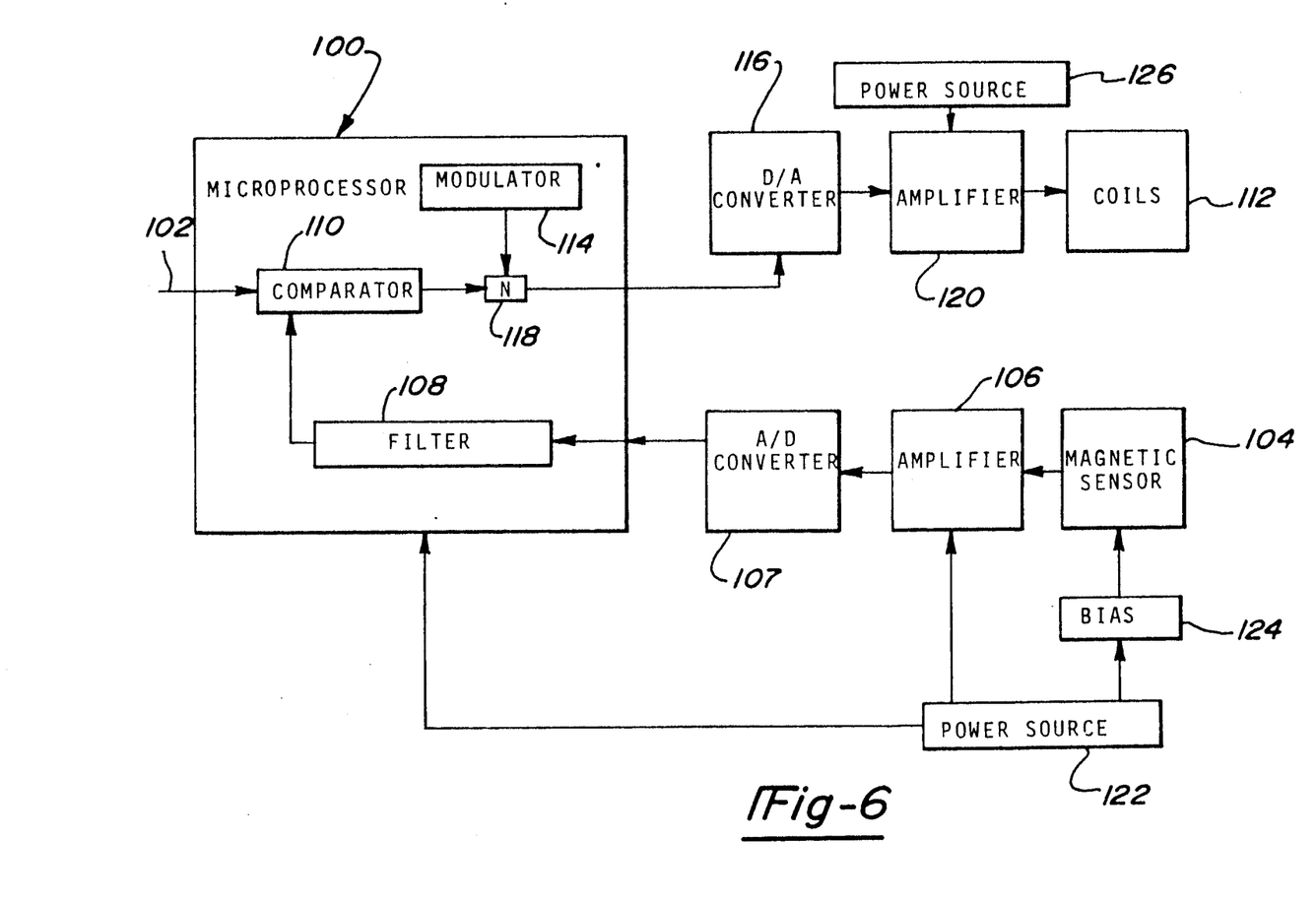
FIG. 6 is a block diagram of an embodiment of the present invention in which the circuit of the inventive apparatus is arbitrarily divided into convenient functional sections.

Referring now to FIG. 6 of the drawings, a block diagram is shown which depicts one preferred arrangement of the circuits of cartilage growth regulator 20 in functional segments. Numerous other circuit arrangements may be possible if the principles of the present invention are faithfully observed. Microcontroller or microprocessor 100 is seen by which the composite magnetic field is maintained at a constant predetermined level despite changes in the ambient component as previously described. In this respect, input 102 is provided by which a set point value of the predetermined composite magnetic flux density along a predetermined axis through the target tissue is input into microprocessor 100. As will be shown, the composite field strength is compared to this set point value to generate an error equal to the difference in the set point value and the measured value of the composite magnetic flux density along the axis.

Magnetic field sensor 104 is provided by which the magnitude of the composite field which passes through the target tissue along the axis is measured. It is preferred that magnetic field sensor 104 comprise a Hall-effect device which, as will be known by those skilled in the art, produces an analog signal. The magnetic field sensor 104 constantly monitors the composite magnetic field, sending a signal to microprocessor 100. It will be understood that the output of a Hall-effect magnetic sensor is relatively small; thus, magnetic field sensor amplifier 106 is provided by which the signal from magnetic field sensor 104 is amplified, for example, up to three thousand times its original value. Since a Hall-effect device produces an analog signal, analog-to-digital converter 107 is provided by which the amplified signal from magnetic field sensor 104 is converted to a digital signal which can be used by microprocessor 100. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 106 which is input into microprocessor 100 is filtered by software filter 108 to remove shot noise and sudden fluctuations in the composite field detected by magnetic field sensor 104. Although it is preferred that filter 108 comprise software in microprocessor 100, a discrete filter could be used. In this embodiment, software filter 108 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of cartilage growth regulator 20 with respect to the ambient field component. Hence, the time constant of filter 108 should be such that momentary fluctuations are filtered out.

Microprocessor 100 includes logic which calculates the non-zero net average value of the composite magnetic flux density. This non-zero average value is then compared at comparator 110 in microprocessor 100 to the predetermined dc reference or offset value which is input into microprocessor 100 via input 102. It should be noted that this reference value is preferably established by dedicated circuitry in microprocessor 100, although variable input means could be included by which the set point value could be changed. An error statement is then generated defining the difference in the measured value of the composite magnetic flux density and the set point or reference value. Microprocessor 100 then determines the magnitude of the output necessary to drive magnetic field generating coils 112 to bring the composite magnetic flux density back to the set point.

Software field modulator or oscillator 114 is provided by which an ac or fluctuating component is superimposed on the digital output signal which is input into digital-to-analog converter 116. From the previous discussion of the present invention, it will be understood that software field modulator 114 of microprocessor 100 in the preferred embodiment of the present invention is preset to a fixed, predetermined frequency to produce the desired predetermined, growth-regulating ratio of frequency-to-magnetic flux density value. In another embodiment, the feedback system of the present invention is such that changes in the composite magnetic flux density are measured, whereupon microprocessor 100 determines the necessary change in frequency to maintain the predetermined relationship. In that embodiment, software field modulator 114 produces the requisite ac frequency. It is again preferred that digital-to-analog converter 116 be provided on-board the microprocessor chip. Hence, software field modulator 114 provides the ac component at node 118.

The signal from digital-to-analog converter 116 is fed to voltage-to-current amplifier 120, the output of which drives magnetic field generating coils 112 in the desired manner. Hence, the composite field is held substantially constant despite changes in the ambient component.

While several arrangements of power sources are suitable, it is preferred that power supply 122 be provided to power magnetic field sensor amplifier 106, microprocessor 100 and magnetic field sensor 104, the latter via bias circuitry 124. A separate power source 126 is preferred for voltage to current amplifier 120.

Having fully described the apparatus of the present invention, including its manner of construction, operation and use, the method of the present invention will now be described. It is to be understood that this description of the method incorporates the foregoing discussion of the novel apparatus. In this aspect, the present invention provides a method of regulating the growth characteristics of cartilaginous tissue. This is achieved in one embodiment by generating a fluctuating, directionally-oriented magnetic field which projects through the target cartilage. The magnetic field generating means preferred for use is cartilage growth regulator 20 previously described. The magnetic field so generated has a magnetic flux density of precisely controlled parameters which passes through the target tissue parallel to a predetermined axis projecting through the tissue. As will be known by those skilled in art and as has been clearly explained, the local magnetic field to which the target tissue is subjected will have a component which is parallel to the predetermined axis and which thus aids or opposes the applied or generated magnetic field along the axis. At times, the local component may be zero. In the method of the present invention, the density of this combined magnetic flux, and more specifically the average non-zero value of the combined magnetic flux density, is controlled to provide a precise relationship between the flux density along the axis and the frequency of the applied magnetic field which is oscillating at a predetermined value. Most preferably this is accomplished by adjusting the intensity of the applied field to compensate for changes in the local field. Thus, in one embodiment, the present invention provides a method of regulating growth characteristics of living cartilage by creating a magnetic field which penetrates the tissue and which has a predetermined relationship between frequency of oscillation and average flux density. The predetermined relationship or ratio of frequency-to-field magnitude is determined with reference to the equation:

$$f_c/B = q/(2\pi m)$$

where $f_c$ is the frequency of the combined magnetic field along the predetermined axis in Hertz, B is non-zero net average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla.

In order to create this fluctuating magnetic field having the desired parameters, the composite magnetic field parallel to the predetermined axis is repetitively monitored. As stated, this is preferably carried out with a Hall effect device or the like which produces an analog signal. This analog signal is periodically sampled by microprocessing means which then calculates the necessary frequency and/or magnitude of the applied magnetic field to maintain the preprogrammed, predetermined ratio previously described. Of course, it will now be understood that it is the combined magnetic flux which is sensed by the magnetic field sensor. The magnetic field generating means is used to adjust the magnitude of this composite field where appropriate.

In one embodiment, the method includes controlling the average value of the applied magnetic flux density along a predetermined axis to maintain a predetermined ratio of frequency-to-composite magnetic flux density. In another embodiment, the frequency of the fluctuations is adjusted to maintain this relationship in which changes in the combined magnetic flux density due to changes in the local magnetic field are detected. Moreover, a combination of these two methods may be used wherein both the frequency and the magnitude of the magnetic field flux density are adjusted to maintain the predetermined relationship of the present invention.

Hence, the method of the present invention includes the steps of creating and maintaining a predetermined relationship between the frequency of a fluctuating magnetic field to the flux density of the field. In particularly preferred embodiments, a frequency of 16 Hertz and an average flux density of $2.09 \times 10^{-5}$ Tesla are utilized. This combination of frequency and flux density is particularly useful in promoting growth of cartilaginous tissue. Another preferred frequency and corresponding flux density which is useful in stimulating the growth of cartilage is 16 Hertz and $1.27 \times 10^{-5}$ Tesla.

In a preferred embodiment of the method of the present invention, the ratio of frequency-to-flux density is determined by selecting a preselected ion present in the biological fluids associated with the cartilaginous tissue which is to be stimulated by the present invention and tuning the fluctuating composite magnetic flux density to the specific cyclotron resonance frequency for the ion. The preferred ions for stimulating growth of cartilaginous tissue are $Ca^{++}$ and $Mg^{++}$. Ions which may be useful in the present invention are set forth in the following table for purposes of illustration and not limitation:

Hydrogen, $H^+$
Lithium, $Li^+$
Sodium, $Na^+$
Chlorine, $Cl^-$
Bicarbonate, $HCO^-_3$ Hence, in addition to the apparatus of the present invention, the present invention provides a method for controlling growth characteristics of cartilaginous tissue which includes the steps of creating a fluctuating magnetic field of predetermined frequency and flux density along an axis projecting through a predetermined volume and positioning a region of cartilage such as damaged hyaline cartilage, fibrocartilage, or elastic cartilage within this predetermined space such that it is exposed to the fluctuating magnetic field. The predetermined parameters of the fluctuating magnetic field are determined by measuring the net average value of the combined magnetic flux density parallel to the predetermined axis through the tissue, where the combined magnetic field is the sum of the local magnetic field along the predetermined axis and the applied magnetic field. The frequency and/or magnitude of the applied magnetic flux density is then adjusted to produce a combined magnetic field along the axis having a predetermined ratio of frequency-to-flux density. This predetermined ratio influences the growth characteristics of the target tissue. The tissue is exposed to the fluctuating magnetic field for a duty cycle and a period of time sufficient to properly affect the growth characteristics of the tissue, stimulating the regeneration of the damaged cartilage in the preferred embodiment.

The following examples are provided to further describe and illustrate the present invention and are in no way intended to limit the scope of the appended claims.

EXAMPLE A

Forty-eight chick embryos were cultured in ovo for 8 days in a standard egg incubator at 39 degrees C. and 100% humidity. At the end of the eight days, the embryos were removed to a petri dish, and the inferior extremities were removed by blunt dissection. the femurs from the legs were then removed, also by blunt dissection, and retained as pairs on sterile gauze surgical sponges moistened with Hanks' Balanced Salt Solution (HBSS). The paired femurs were then removed to $6 \times 6$ cm squares of sterile dry unbleached muslin. Each bone was rolled back and forth on the muslin to remove adherent tissues. When the cleaning was complete, each bone was placed in the appropriate numbered well of a Linbro 12-well culture dish in a manner which ensured that each femur could be identified individually as to its embryo of origin. The wells contained a stainless steel support screen topped by a triangular piece of sterile lens tissue. The wells were filled with Fitton-Jackson's modification of BGJb medium to the point where a meniscus of medium was present at the surface of the lens tissue. This method of culture ensured adequate nutrition and gas exchange for the explanted femurs. Growth was essentially normal in the controls.

Control plates containing the left femurs were placed in an incubator at 37 degrees C. in 5% $CO_2$/air at 100% humidity. Experimental plates containing the right femurs were similarly incubated, except that they were placed into an incubator chamber containing a tissue growth apparatus in accordance with the principles of the present invention. The coils were energized to produce a static ($B_o$) field of $12.68 \times 10^{-6}$ T at 16 Hz and at an ac amplitude of $15 \times 10^{-6}$ T. The fields generated passed through the explants parallel to the surface of the medium in the wells. The field parameters satisfied the conditions for resonance of the Magnesium ion, according to the cyclotron resonance formula.

The control and experimental cultures were maintained for 7 days and were then harvested. The femurs were fixed in Millonig's neutral buffered formalin for 24 hours and were then measured for length and diameter. Following the measurements, the femurs were embedded in paraffin, sectioned at 5 microns, and stained with Hematoxylin and Eosin for histological comparison.

The experimental femurs averaged $8.4 + -0.8$ mm in length, while the controls averaged only $7.6 + -0.5$ mm in length. Thus the experimental femurs exhibited an increase in length of approximately 11% over the controls ($p<0.001$). The diameter of the experimental femurs averaged $1.1 + -0.1$ mm, while the controls averaged only $0.8 + -0.7$ mm. Thus, the experimentals were approximately 38% thicker than the controls, a figure which was highly significant ($p<0.0001$). Upon microscopic examination, the experimental femurs were revealed to be essentially identical in histological appearance to the controls, except for the greater mass of cartilage and a concomitantly larger bony diaphyseal collar. The collar length of the experimental femurs was 63% greater than the controls (1.86 vs. 1.14 mm $p<0.001$) and the thickness was 67% greater (0.15 vs. 0.21 mm $p<0.001$). Assuming essentially cylindrical bones, the volume ($\frac{1}{2}pi \times r^2 \times H$) of the experimental femurs was 109% greater than the controls, again a highly significant ($p<0.0001$) value. Most of this increase was obviously in the form of cartilage, given the slight volume of the bony diaphyseal collar.

Thus, when the methods of the present invention are employed, a significant increase in the mass of cartilage formed in a developing system can be achieved such that cartilage mass can be increased where desired, as in the case of slowed or arrested growth of the epiphyseal plate.

In a second experiment, twelve adult (>2 Kg) New Zealand White rabbits of mixed sex were subjected to left fibular ostectomies. The rabbits were anaesthetized, and the left and right fibulae were exposed surgically. The periosteum was reflected from the fibulae of both sides. On the right side, the periosteum was allowed to return to its original position. On the left side, a 1 cm long piece of bone was removed from the fibula approximately 1 cm proximal to the union of the fibula with the tibia. There, periosteum was again allowed to return to its original position, and the wounds were closed with Dexon absorbable sutures.

Six of the animals were returned to normal cages, and no further treatment was given for the period of the experiment. These animals served as the controls. The other six animals were removed to cages which were equipped with cartilage growth apparatuses which employed the principles of the present invention. The cartilage growth apparatuses were positioned so as to deliver an ac magnetic field perpendicular to the earth's surface. The coils were energized to provide a static field of $40 \times 10^{-6}$ T, an ac field of $15 \times 10^{-6}$ T, and a frequency of 50.5 Hz. The fields penetrated the animals perpendicular to their craniocaudal axes, and satisfied the conditions for Magnesium ion resonance according to the cyclotron resonance formula. The experimental animals were exposed to the fields for a period of ½ hour per day for 30 days. All animals were watered and fed ad libitum. The temperature of the animal rooms was maintained at 23 degrees C. and 55% humidity, with a light cycle of 14/10 hr on/off.

At the end of the 30 day period, the animals were sacrificed by $CO_2$ inhalation, and the legs were disarticulated at the knee and ankle and removed. The gastrocnemius/soleus/plantaris complex of muscles was then removed. Radiographs were taken in the P-A axis by placing the paired right and left fibulae directly onto a film cassette, so that the fibulae were clearly and distinctly separated from the tibiae in the developed films. The diameters of the regenerated calluses were then obtained to the nearest 0.1 mm by the use of digital metric calipers.

The calluses of the experimental animals were approximately 50% greater in diameter than the controls (41 vs. 27 mm, $p < 0.01$). The callus volume increased by 131% ($p < 0.001$). The calluses were also significantly (+85%, $p < 0.01$) stiffer.

Thus, the use of the methods of the present invention can also enhance the formation of cartilage for regenerative responses, such as in bone repair, and correcting joint trauma.

While a particular embodiment of this invention is shown and described herein, it will be understood, of course, that the invention is not to be limited thereto since many modifications may be made, particularly by those skilled in this art, in light of this disclosure. It is contemplated therefore by the appended claims to cover any such modifications that fall within the true spirit and scope of this invention.

What is claimed is:

1. A method for regulating the growth characteristics of cartilage, said cartilage being subject to an ambient magnetic field, comprising the steps of:
   positioning magnetic field generating means adjacent a living subject such that a region of cartilage of said subject occupies a predetermined space, said region of cartilage being subject to an ambient magnetic field;
   generating an applied magnetic flux with said magnetic field generating means, said applied magnetic flux extending through said region of cartilage parallel to a predetermined axis projecting through said predetermined spaced and combining with said ambient magnetic field to form a composite magnetic flux; and
   fluctuating said applied magnetic flux and controlling the average value of the magnetic flux density of said combined magnetic flux to create and maintain a predetermined relationship between the frequency of said fluctuations and the magnitude of said magnetic flux density, wherein said average value of said magnetic flux density is a non-zero average value, and wherein said predetermined relationship regulates development of said cartilage, said predetermined relationship being a function of the cyclotron resonance frequency of a predetermined ion present in said cartilage.

2. The method recited in claim 1, wherein said predetermined relationship of said frequency to said magnitude of said magnetic flux density is determined using the equation $$f_c/B = q/(2\pi m)$$

where $f_c$ is said frequency in Hertz, B is the average value of said combined magnetic flux density in Tesla parallel to said predetermined axis, and q/m has a value of from about $5 \times 10^5$ to about $100 \times 10^6$ in Coulombs per kilogram and where B preferably has a value not in excess of about $5 \times 10^{-4}$ Tesla.

3. The method recited in claim 2, wherein q and m are, respectively, equal to the charge and mass of a preselected ionic species.

4. The method recited in claim 3, wherein said preselected ionic species is selected from the group consisting of $Ca^{++}$ and $Mg^{++}$ and said regulation of the development of said cartilage is an increase in the rate of growth.

5. The method recited in claim 2, wherein said function of said cyclotron resonance frequency is a harmonic of fc.

6. The method recited in claim 1, wherein said cartilage is selected from the group consisting of hyaline cartilage, fibrocartilage and elastic cartilage.

* * * * *